US011183304B2

United States Patent
Kochura et al.

(10) Patent No.: US 11,183,304 B2
(45) Date of Patent: Nov. 23, 2021

(54) PERSONALIZED SMART HOME RECOMMENDATIONS THROUGH COGNITIVE LOAD ANALYSIS

(71) Applicant: International Business Machines Corporation, Armonk, NY (US)

(72) Inventors: Nadiya Kochura, Bolton, MA (US); Donna K. Byron, Petersham, MA (US); Fang Lu, Billerica, MA (US); Vibha Anand, Cambridge, MA (US)

(73) Assignee: International Business Machines Corporation, Armonk, NY (US)

( * ) Notice: Subject to any disclaimer, the term of this patent is extended or adjusted under 35 U.S.C. 154(b) by 197 days.

(21) Appl. No.: 16/242,137

(22) Filed: Jan. 8, 2019

(65) Prior Publication Data

US 2020/0219620 A1    Jul. 9, 2020

(51) Int. Cl.
*G16H 50/30* (2018.01)
*G06N 7/08* (2006.01)
*G08B 21/04* (2006.01)
*G06N 20/00* (2019.01)
*G08B 21/18* (2006.01)

(52) U.S. Cl.
CPC .............. *G16H 50/30* (2018.01); *G06N 7/08* (2013.01); *G06N 20/00* (2019.01); *G08B 21/0423* (2013.01); *G08B 21/0453* (2013.01); *G08B 21/182* (2013.01)

(58) Field of Classification Search
CPC .......... G16H 50/30; G06N 20/00; G06N 7/08; G08B 21/0423; G08B 21/0453; G08B 21/182
USPC ....................................................... 702/127
See application file for complete search history.

(56) References Cited

U.S. PATENT DOCUMENTS

| | | | |
|---|---|---|---|
| 8,275,348 B2 | 9/2012 | Yen et al. | |
| 9,501,919 B2 * | 11/2016 | Laett | .............. G16H 30/40 |
| 9,846,999 B1 | 12/2017 | Pickover et al. | |
| 10,028,675 B2 * | 7/2018 | Patel | ................... A61B 5/0022 |
| 10,140,833 B1 * | 11/2018 | Jacobson | .............. A61B 5/744 |
| 10,564,422 B1 * | 2/2020 | Bevilacqua | ......... G06F 3/1423 |
| 2008/0007418 A1 | 1/2008 | Maki et al. | |

(Continued)

OTHER PUBLICATIONS

P. Pirzada, N. White and A. Wilde, "Sensors in Smart Homes for Independent Living of the Elderly," 2018 5th International Multi-Topic ICT Conference (IMTIC), Jamshoro, 2018, pp. 1-8, doi: 10.1109/IMTIC.2018.8467234) (Year: 2018).*

Anonymous, "Drone Airbag for Fall Amelioration," An IP.com Prior Art Database Technical Disclosure, No. IPCOM000244386D, Published Dec. 8, 2015, 5 pages.

(Continued)

*Primary Examiner* — Catherine T. Rastovski
*Assistant Examiner* — Aeysha N Sultana
(74) *Attorney, Agent, or Firm* — Yee & Associates, P.C.

(57) ABSTRACT

A method and system for preventing falls and accidents is provided comprising. A user's location and movement are monitored by a number of input devices. The user's activities are also monitored by a number of input devices. Potential dangers are identified within a first specified proximity of the user, and a determination is made if the user's current activity indicates a cognitive load that exceeds a predefined threshold. In response to identification of a potential danger within the first specified proximity and a concurrent determination that the user's cognitive load exceeds the threshold, a number of devices within a second specified proximity of the user are activated to alert the user of the potential danger.

17 Claims, 5 Drawing Sheets

(56) References Cited

U.S. PATENT DOCUMENTS

| | | | |
|---|---|---|---|
| 2010/0049096 A1 | 2/2010 | Ten Kate | |
| 2010/0196861 A1 | 8/2010 | Lunner | |
| 2011/0251520 A1* | 10/2011 | Shieh | A61B 5/7275 |
| | | | 600/587 |
| 2012/0095722 A1 | 4/2012 | Ten Kate | |
| 2015/0248532 A1* | 9/2015 | Rajasenan | G16H 40/20 |
| | | | 705/2 |
| 2016/0293024 A1* | 10/2016 | Kozloski | G06Q 10/109 |
| 2016/0369504 A1 | 12/2016 | Kim et al. | |
| 2017/0000387 A1* | 1/2017 | Forth | G06N 7/005 |
| 2017/0140631 A1* | 5/2017 | Pietrocola | G08B 31/00 |
| 2017/0151081 A1 | 6/2017 | Feris et al. | |
| 2018/0228405 A1* | 8/2018 | Burwinkle | A61B 5/0002 |
| 2019/0307384 A1* | 10/2019 | Baeuerle | A61B 5/1123 |

OTHER PUBLICATIONS

Majumder et al., "A Multi-Sensor Approach for Fall Risk Prediction and Prevention in Elderly," Applied Computing Review, Mar. 2014, vol. 14, No. 1, pp. 41-52.

Wu et al., "Understanding Older Users' Acceptance of Wearable Interfaces for Sensor-based Fall Risk Assessment," Proceedings of the 2018 CHI Conference on Human Factors in Computing Systems (CHI '18), Apr. 21-26, 2018, Montreal, QC, Canada, Paper 119, 13 pages.

Herman et al., "Executive Control Deficits as a Prodrome to Falls in Healthy Older Adults: A Prospective Study Linking Thinking, Walking, and Falling," Journal of Gerontology: Medical Sciences, Oct. 2010, vol. 65A, Issue 10, pp. 1086-1092.

* cited by examiner

PERSONALIZED SMART HOME RECOMMENDATIONS THROUGH COGNITIVE LOAD ANALYSIS

BACKGROUND

The disclosure relates generally to safety systems, and more specifically to a method and system for monitoring user activity for signs of cognitive overload that increase the risk of falls or injury and alerting the user to regain attention.

The risk of falls increases in older populations, presenting a significant public health problem with substantial impact on health and healthcare costs. Falls are one of the most common geriatric syndromes, threatening the independence of older persons. They are the leading cause of injuries and disabilities among the aged population. Unintentional falls are one of the most costly and complex health issues facing older persons around the world.

Cognition is an important contributor to safe mobility through one's environment. Although physical abilities such as balance and strength undoubtedly factor into one's capacity to be mobile, specific cognitive processes such as attention, planning, and decision making collectively ensure safety during movement.

However, high cognitive load and distraction in the elderly has been shown to affect their center of balance. With the increased cognitive load being placed on the general population, including the elderly, through the use of increasingly ubiquitous electronic devices, the risk of falls is increasing. Interestingly, this type of cognitive overload and distraction is even being exhibited in much younger people who are inundated with seemingly endless streams of information. A common example is someone walking into a crosswalk or intersection without looking around to check for oncoming traffic or accidentally mis-stepping off a curb while using a mobile telephone.

SUMMARY

A method for preventing falls and accidents, comprising: monitoring, by a number of input devices, a user's location and movement; monitoring, by a number of input devices, the user's activities; identifying, by a number of processors in communication with the input devices, potential dangers within a first specified proximity of the user; determining, by a number of processors in communication with the input devices, if the user's current activity indicates a cognitive load that exceeds a predefined threshold; and in response to identification of a potential danger within the first specified proximity and a concurrent determination that the user's cognitive load exceeds the threshold, activating, by a number of processors, a number of devices within a second specified proximity of the user to alert the user of the potential danger.

A system for preventing falls and accidents, comprising: a bus system; a storage device connected to the bus system, wherein the storage device stores program instructions; and a number of processors connected to the bus system, wherein the processors execute the program instructions to: monitor a user's location and movement from data provided by a number of input devices; monitor the user's activities from data provided by a number of input devices; identify, according to data provided by the input devices, potential dangers within a first specified proximity of the user; determine, according to data provided by the input devices, if the user's current activity indicates a cognitive load that exceeds a predefined threshold; and in response to identification of a potential danger within the first specified proximity and a concurrent determination that the user's cognitive load exceeds the threshold, activate a number of devices within a second specified proximity of the user to alert the user of the potential danger.

A computer program product for preventing falls and accidents, comprising, the computer program product comprising a non-volatile computer readable storage medium having program instructions embodied therewith, the program instructions executable by a computer to cause the computer to perform the steps of: monitoring a user's location and movement from data provided by a number of input devices; monitoring the user's activities from data provided by a number of input devices; identifying, according to data provided by the input devices, potential dangers within a first specified proximity of the user; determining, according to data provided by the input devices, if the user's current activity indicates a cognitive load that exceeds a predefined threshold; and in response to identification of a potential danger within the first specified proximity and a concurrent determination that the user's cognitive load exceeds the threshold, activating a number of devices within a second specified proximity of the user to alert the user of the potential danger.

DETAILED DESCRIPTION

Aspects of the present invention are described herein with reference to diagrams of methods and apparatuses according to embodiments of the invention. The diagrams in the Figures illustrate the architecture and operation of possible implementation methods according to various embodiments of the present invention.

Illustrative embodiments take advantage of the growing Internet of Things (IoT) to provide a new method to build a real-time monitoring system that monitors user location and cognitive load relative to potential dangers in the vicinity. Predictive models allow the system to determine if the cognitive load is likely to increase fall or injury risk and activates alerting devices in the vicinity of the user to bring the user's attention back to the present of the surroundings.

By using various sensor data to monitor user activity and cognitive load, the system identifies cognitive load thresholds. The system determines a risk of falling score and dynamically adjusts this score based on the evaluation of current cognitive load. The system analyzes the adjusted risk score and applies smart home features to help the person overcome a cognitive overload state and prevent falling.

As used herein, the phrase "a number" means one or more. The phrase "at least one of", when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category.

For example, without limitation, "at least one of item A, item B, or item C" may include item A, item A and item B, or item C. This example also may include item A, item B, and item C or item B and item C. Of course, any combinations of these items may be present. In some illustrative examples, "at least one of" may be, for example, without limitation, two of item A; one of item B; and ten of item C; four of item B and seven of item C; or other suitable combinations.

Figure 1:
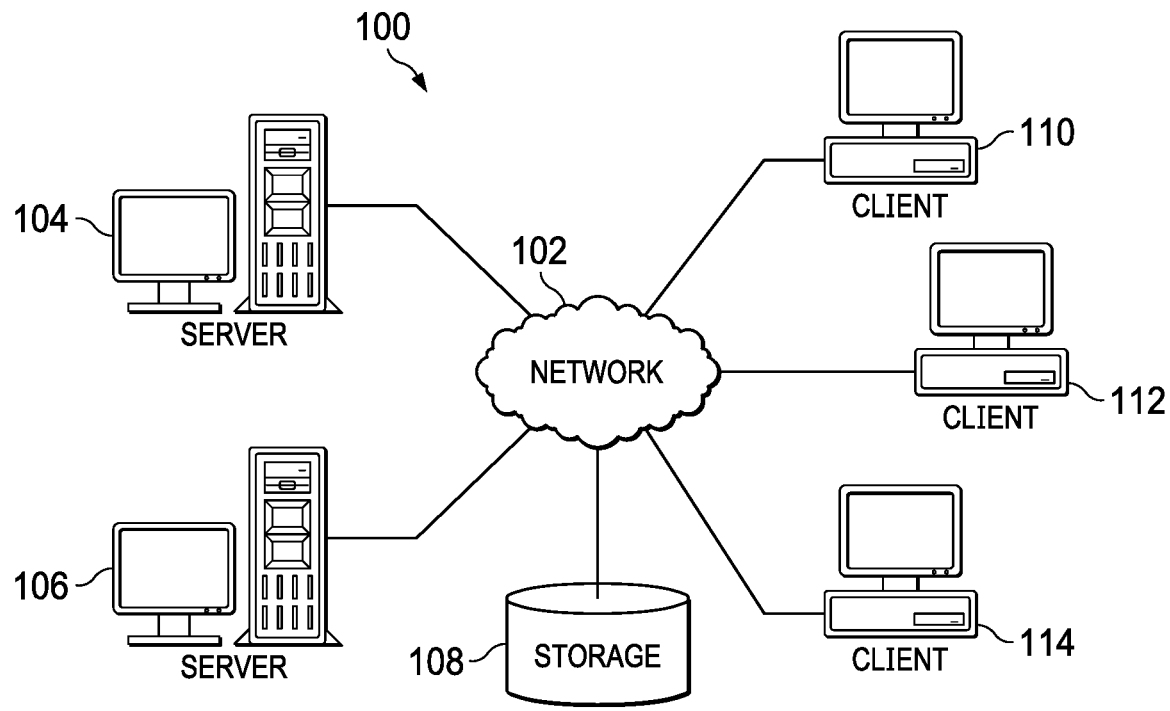
FIG. 1 depicts a pictorial representation of a network of data processing systems in which illustrative embodiments can be implemented.

FIG. 1 depicts a pictorial representation of a network of data processing systems in which illustrative embodiments can be implemented. Network data processing system 100 is a network of computers, data processing systems, and other devices in which the illustrative embodiments may be implemented. Network data processing system 100 contains network 102, which is the medium used to provide communications links between the computers, data processing systems, and other devices connected together within network data processing system 100. Network 102 may include connections, such as, for example, wire communication links, wireless communication links, and fiber optic cables.

In the depicted example, server 104 and server 106 connect to network 102, along with storage 108. Server 104 and server 106 may be, for example, server computers with high-speed connections to network 102. In addition, server 104 and server 106 may provide a set of one or more connector services for managing idempotent operations on a system of record, such as storage 108. An idempotent operation is an identical operation, which was previously performed, that has the same effect as performing a single operation. Also, it should be noted that server 104 and server 106 may each represent a plurality of servers providing management of idempotent operations for a plurality of system of records.

Client 110, client 112, and client 114 also connect to network 102. Clients 110, 112, and 114 are clients of server 104 and server 106. Server 104 and server 106 may provide information, such as boot files, operating system images, and software applications to clients 110, 112, and 114.

In this example, clients 110, 112, and 114 are shown as desktop or personal computers. However, it should be noted that clients 110, 112, and 114 are intended as examples only. In other words, clients 110, 112, and 114 may include other types of data processing systems, such as, for example, network computers, laptop computers, tablet computers, handheld computers, smart phones, smart watches, personal digital assistants, gaming devices, set-top boxes, kiosks, and the like. Users of clients 110, 112, and 114 may utilize clients 110, 112, and 114 to access system of records corresponding to one or more enterprises, via the connector services provided by server 104 and server 106, to perform different data operations. The operations may be, for example, retrieve data, update data, delete data, store data, and the like, on the system of records.

Storage 108 is a network storage device capable of storing any type of data in a structured format or an unstructured format. In addition, storage 108 may represent a plurality of network storage devices. Further, storage 108 may represent a system of record, which is an authoritative data source, corresponding to an enterprise, organization, institution, agency, or similar entity. Furthermore, storage unit 108 may store other types of data, such as authentication or credential data that may include user names, passwords, and biometric data associated with client users and system administrators, for example.

In addition, it should be noted that network data processing system 100 may include any number of additional servers, clients, storage devices, and other devices not shown. Program code located in network data processing system 100 may be stored on a computer readable storage medium and downloaded to a computer or other data processing device for use. For example, program code may be stored on a computer readable storage medium on server 104 and downloaded to client 110 over network 102 for use on client 110.

In the depicted example, network data processing system 100 may be implemented as a number of different types of communication networks, such as, for example, an internet, an intranet, a local area network (LAN), and a wide area network (WAN). FIG. 1 is intended as an example only, and not as an architectural limitation for the different illustrative embodiments.

There are three main categories of machine learning: supervised, unsupervised, and reinforcement learning. Supervised machine learning comprises providing the machine with training data and the correct output value of the data. During supervised learning the values for the output are provided along with the training data (labeled dataset) for the model building process. The algorithm, through trial and error, deciphers the patterns that exist between the input training data and the known output values to create a model that can reproduce the same underlying rules with new data. Examples of supervised learning algorithms include regression analysis, decision trees, k-nearest neighbors, neural networks, and support vector machines.

If unsupervised learning is used, not all of the variables and data patterns are labeled, forcing the machine to discover hidden patterns and create labels on its own through the use of unsupervised learning algorithms. Unsupervised learning has the advantage of discovering patterns in the data with no need for labeled datasets. Examples of algorithms used in unsupervised machine learning include k-means clustering, association analysis, and descending clustering.

Whereas supervised and unsupervised methods learn from a dataset, reinforcement learning methods learn from interactions with an environment. Algorithms such as Q-learning are used to train the predictive model through interacting with the environment using measurable performance criteria.

Figure 2:
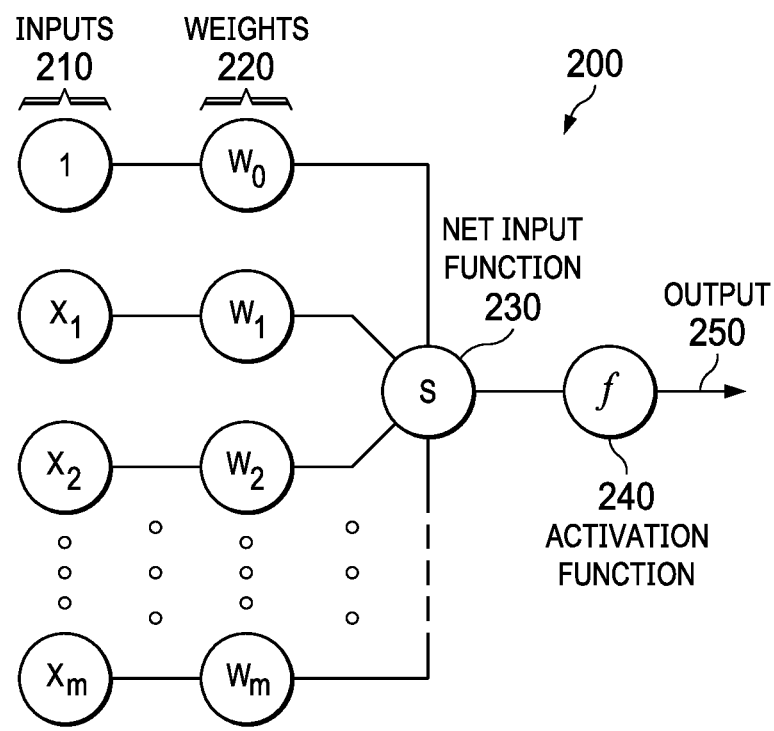
FIG. 2 is a diagram that illustrates a node in a neural network in which illustrative embodiments can be implemented.

FIG. 2 is a diagram that illustrates a node in a neural network in which illustrative embodiments can be implemented. Node 200 combines multiple inputs 210 from other nodes. Each input 210 is multiplied by a respective weight 220 that either amplifies or dampens that input, thereby assigning significance to each input for the task the algorithm is trying to learn. The weighted inputs are collected by a net input function 230 and then passed through an activation function 240 to determine the output 250. The connections between nodes are called edges. The respective weights of nodes and edges might change as learning proceeds, increasing or decreasing the weight of the respective signals at an edge. A node might only send a signal if the aggregate input signal exceeds a predefined threshold. Pairing adjustable weights with input features is how significance is assigned to those features with regard to how the network classifies and clusters input data.

Neural networks are often aggregated into layers, with different layers performing different kinds of transformations on their respective inputs. A node layer is a row of nodes that turn on or off as input is fed through the network. Signals travel from the first (input) layer to the last (output) layer, passing through any layers in between. Each layer's output acts as the next layer's input.

Stochastic neural networks are a type of network that incorporate random variables, which makes them well suited for optimization problems. This is done by giving the nodes in the network stochastic (randomly determined) weights or transfer functions. A Boltzmann machine is a type of stochastic neural network in which each node is binary valued, and the chance of it firing depends on the other nodes in the network. Each node is a locus of computation that processes an input and begins by making stochastic decisions about whether to transmit that input or not. The weights (coefficients) that modify inputs are randomly initialized.

Boltzmann machines optimize weights and quantities and are particularly well suited to represent and solve difficult combinatorial problems. To solve a learning problem, a Boltzmann machine is shown a set of binary data vectors and must find weights on the connections so that the data vectors are good solutions to the optimization problem defined by those weights.

Figure 3:
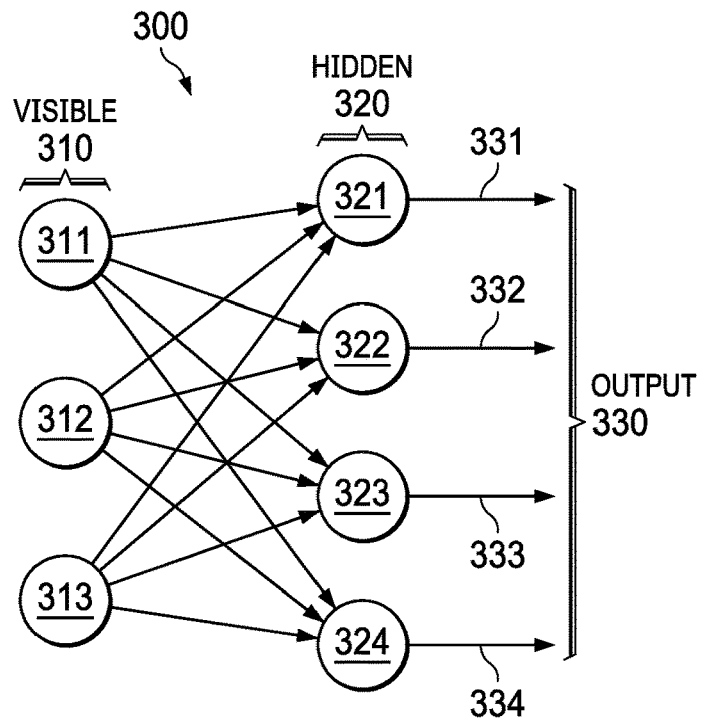
FIG. 3 is a diagram illustrating a restricted Boltzmann machine in which illustrative embodiments can be implemented.

FIG. 3 is a diagram illustrating a restricted Boltzmann machine in which illustrative embodiments can be implemented. As shown in FIG. 3, the nodes in the Boltzmann machine 300 are divided into a layer of visible nodes 310 and a layer of hidden nodes 320. A common problem with general Boltzmann machines is that they stop learning correctly when they are scaled up. Restricted Boltzmann machines (RBMs) overcome this problem by using an architecture that does not allow connections between nodes in the same layer. As can be seen in FIG. 3, there is no intralayer communication between nodes.

The visible nodes 310 are those that receive information from the environment (i.e. a set of external training data). Each visible node in layer 310 takes a low-level feature from an item in the dataset and passes it to the hidden nodes in the next layer 320. When a node in the hidden layer 320 receives an input value x from a visible node in layer 310 it multiplies x by the weight assigned to that connection (edge) and adds it to a bias b. The result of these two operations is then fed into an activation function which produces the node's output.

In symmetric networks such as Boltzmann machine 300, each node in one layer is connected to every node in the next layer. For example, when node 321 receives input from all of the visible nodes 311-313 each x value from the separate nodes is multiplied by its respective weight, and all of the products are summed. The summed products are then added to the hidden layer bias, and the result is passed through the activation function to produce output 331. A similar process is repeated at hidden nodes 322-324 to produce respective outputs 332-334. In the case of a deeper neural network (discussed below), the outputs 330 of hidden layer 320 serve as inputs to the next hidden layer.

Training a Boltzmann machine occurs in two alternating phases. The first phase is the "positive" phase in which the visible nodes' states are clamped to a particular binary state vector sampled from the training set (i.e. the network observes the training data). The second phase is the "negative" phase in which none of the nodes have their state determined by external data, and the network is allowed to run freely (i.e. the network tries to reconstruct the input). In the negative reconstruction phase the activations of the hidden layer 320 act as the inputs in a backward pass to visible layer 310. The activations are multiplied by the same weights that the visible layer inputs were on the forward pass. At each visible node 311-313 the sum of those products is added to a visible-layer bias. The output of those operations is a reconstruction r (i.e. an approximation of the original input x).

On the forward pass, the RBM uses inputs to make predictions about node activations (i.e. the probability of output given a weighted input x). On the backward pass, the RBM is attempting to estimate the probability of inputs x given activations a, which are weighted with the same coefficients as those used on the forward pass. The bias of the hidden layer helps the RBM to produce activations on the forward pass. Biases impose a floor so that at least some nodes fire no matter how sparse the input data. The visible layer bias helps the RBM learn the reconstructions on the backward pass.

Because the weights of the RBM are randomly initialized the difference between the reconstructions and the original inputs is often large. That error is then backpropagated against the RBM's weights in an iterative learning process, and the weights are adjusted until an error minimum is reached.

In machine learning, a cost function estimates how the model is performing. It is a measure of how wrong the model is in terms of its ability to estimate the relationship between input x and output y. This is expressed as a difference or distance between the predicted value and the actual value. The cost function (i.e. loss or error) can be estimated by iteratively running the model to compare estimated predictions against known values of y during supervised learning. The objective of a machine learning model, therefore, is to find parameters, weights, or a structure that minimizes the cost function.

Gradient descent is an optimization algorithm that attempts to find a local or global minima of a function, thereby enabling the model to learn the gradient or direction that the model should take in order to reduce errors. As the model iterates, it gradually converges towards a minimum where further tweaks to the parameters produce little or zero changes in the loss. At this point the model has optimized the weights such that they minimize the cost function.

As mentioned above, RBMs can be stacked to created deep networks. After training one RBM, the activities of its hidden nodes can be used as training data for a higher level RBM, thereby allowing stacking of RBMs. Such stacking makes it possible to efficiently train several layers of hidden nodes.

Examples of deep networks with which illustrative embodiments can be implemented include, without limitation, Deep Boltzmann Machines (DBM), Deep Belief Networks (DBN), Recurrent Neural Networks (RNN), and Spiking Neural Networks (SNN).

Figure 4:
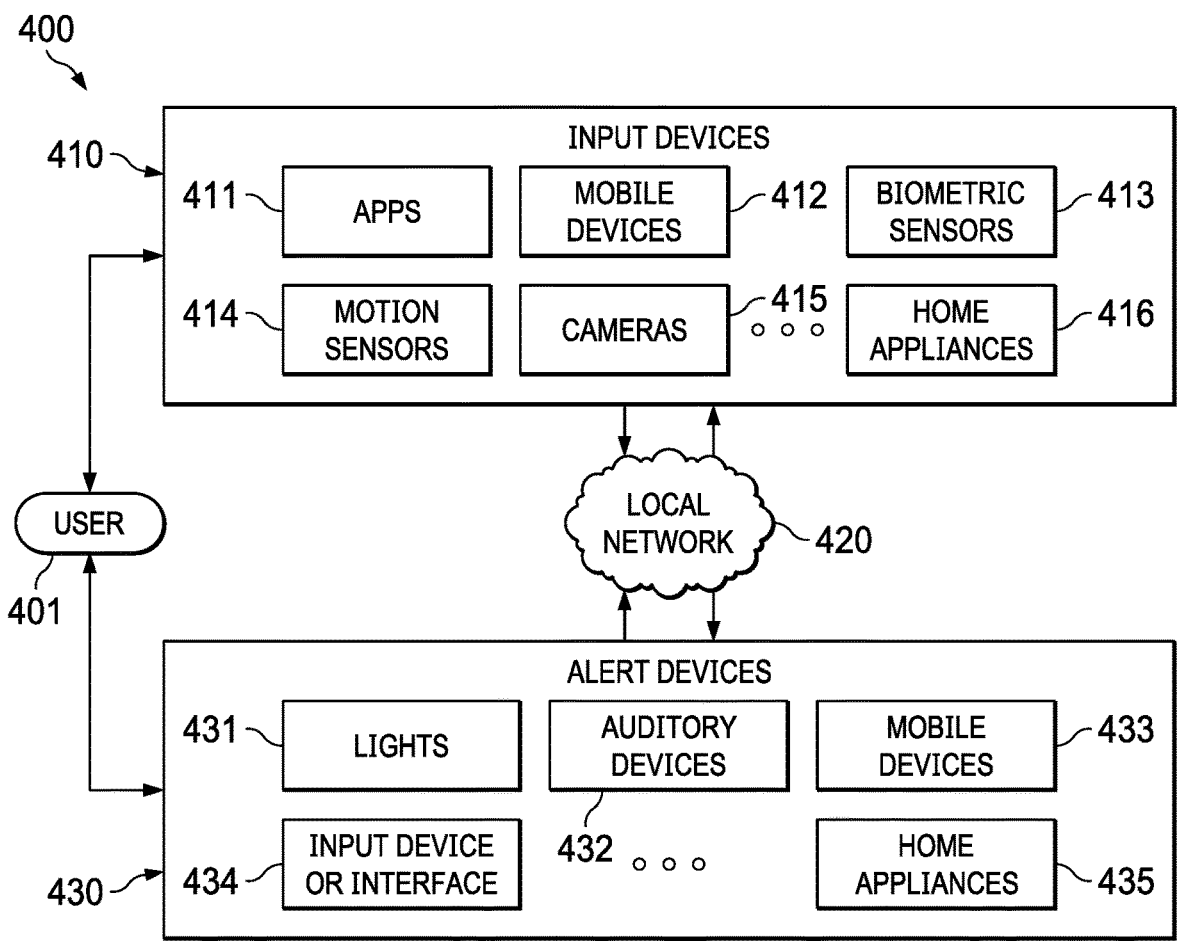
FIG. 4 depicts an architecture for a cognitive load monitoring and alert system 400 in which illustrative embodiments can be implemented.

FIG. 4 depicts an architecture for a cognitive load monitoring and alert system 400 in which illustrative embodiments can be implemented. The monitoring part of the system 400 comprises a number of input devices 410 that are capable of monitoring movements and location of a user 401 and user activities that can contribute to cognitive load. The input devices 410 can comprise any device capable of gathering information about the user's activity and transmitting the data to a data processing system capable of evaluating the data. The input device can include both devices in the user's environment as well as devices that the user 401 is using (and thus are in themselves sources of cognitive load).

In an embodiment, the user's routine environment such a house is mapped and stored in a database and includes the position of objects or features that present potential fall and injury risks within that environment. Example of such potential dangers include, without limitation, stairs, uneven concrete, bathrooms, tubs, stoves, furniture, and fixtures. By monitoring the user's location within the mapped environment, the system 400 can determine if such a potential danger is within a specified proximity of the user 401 at any moment.

Devices that provide data about the user's movement and location within the environment can include motion sensors 414, cameras 415, and mobile devices 412. In the case of motion sensors and cameras the user's location and movement is observed external to the user's activity. In the case of mobile devices such as mobile phones, tablet computers, and similar devices that have location determining capabilities, the user's movement while using such devices is itself the source of the movement and location data. In addition, internet capable ("smart") appliances 416 such as stoves, light fixtures and lamps, refrigerators, televisions, and stereos can provide the system 400 with the user's location by the mere activation of or interaction with an appliance. Biometric sensors such as pedometers worn by the user 401 can also provide movement and location data.

Input devices that provide data regarding the user's cognitive load can include just about any object with which the user 401 interacts that can be configured to transmit information to the system 400. Obvious examples include mobile devices 412, application 411 running on those devices, watching or listening to television or a stereo. However, research has demonstrated that an activity as simple as dexterous manipulation of a device (a seemingly habitual and automatic behavior) involves high order cognitive functions. Therefore, simply carrying and manipulating a mobile device can increase cognitive load even without activating any of its functions. In that vein something as simple as a coffee mug can potentially be equipped with a micro-electro-mechanical system (MEMS) device to both provide data regarding user location and cognitive load. Another example includes a MEMS device embedding in a cooking utensil such as a spatula. Research also indicates that even smell can contribute to cognitive load. Therefore, activities indicative of cooking (e.g., turning on a "smart" stove) can provide data regarding cognitive load as well as potential dangers.

Cognitive load can also be extrapolated from data provided by biometric sensors 413 (either worn by the user or positioned in the environment) including heartrate and body temperature that can be indicative of heightened user activity and therefore increased cognitive load and distraction or alternatively fatigue and impaired cognitive capabilities. Similarly, posture and gait exhibited by the user 401 can be detected by motion sensors 413 and cameras 415. As explained below, such external biometric cure can be correlated with cognitive load.

It should be emphasized that the input devices 410 are not exclusive with regard to their function of providing data regarding location and movement or cognitive load. Such functions can be combined in a single device. A mobile phone is an exemplary example of a single device that simultaneously provide data regarding a user's location, movement, cognitive load, and even act as an alert device (explained below). In situations in which the user 401 is not within a mapped controlled environment, such as walking along a sidewalk, a mobile device with map and location capabilities can provide the system 400 with user location relative to environmental dangers such as intersections, crosswalks, etc., in addition to cognitive load resulting from user dexterous manipulation of and/or interaction with the device such as telephonic activity or application use.

Data from the input devices 410 is fed to a local network 420. The network 420 might comprise network 100 in FIG. 1. It can also comprise one or more neural networks similar to neural network 300 depicted in FIG. 3. Predictive models regarding cognitive load can be employed by the local network 420 to activate alert devices 430 based on data received from the input devices 410.

The alert devices 430 can encompass just about any device or functionality within the user's immediate vicinity capable of being activated to get the user's attention and restore awareness of the immediate environment. In particular, internet capable "smart" appliances 435 within a predetermined proximity to the user 401 and detected environmental danger can be activated to emit a light and/or sound out of the ordinary to get the user's attention and bring the user's focus back to his or her immediate environment and aware from the source of cognitive load. Examples include turning on or flashing a light fixture near a staircase or activating a lamp positioned near a carpet edge. Specialized functions might be added to existing appliances such as specific auditory warnings emitted from a television or stereo speaker. In addition, specialized lights 431 and auditory devices 432 can be placed within the environment to alert the user 401.

Mobile devices 433 can also be used to alert the user 401 to potential dangers within a specified proximity. Such alert can be activated whether the user 401 is specifically using the device or not. In the situation in which the device itself is the source of cognitive load, the alert allows the device to act as its own countermeasure so to speak. The alert can be visual, auditory, or kinesthetic such as vibration.

The alert devices 430 can also include a special input device or interface 434 that require the user 401 to perform a special task (e.g., draw a clock showing a specific time) as a way of probing the user's psychological state and alertness. The special input device 434 can be a standalone device or interface or incorporated into a mobile device or other device or appliance.

In addition to alerting the user in the case of detected cognitive overload, the system can anticipate cognitive overload based on predictive models and alter the manner in which information is delivered to the user without increasing the user's cognitive load. For example, if the user is using a mobile communication device the system can alter the message delivery mechanism based on the user's activities and cognitive load by pausing the message delivery while the user is walking or eating. Alternatively, the system can record message into a voice mail and deliver the message later when the user's cognitive "bandwidth" is sufficient to handle the necessary cognitive load of the new message.

Figure 5:
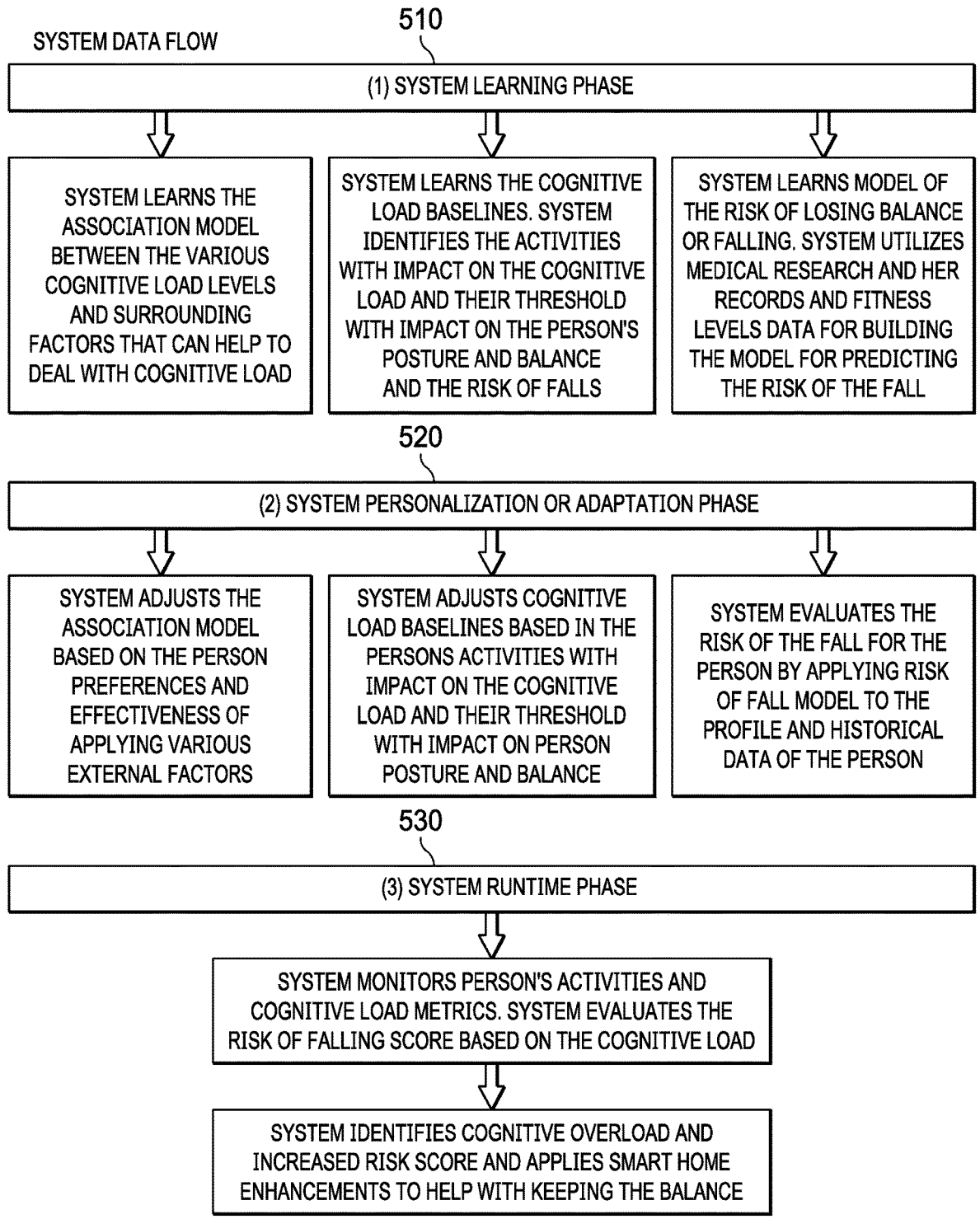
FIG. 5 is a diagram depicting a process for system learning and implementation in accordance with illustrative embodiments.

FIG. 5 is a diagram depicting a process for system learning and implementation in accordance with illustrative embodiments. In an embodiment, the learning process is divided into a system learning phase 510, a system personalization phase 520, and a system runtime phase 530.

In the system learning phase 530 generalized predictive models are constructed based on empirical and population data. In this phase the system learns an association model between various cognitive load levels and surrounding factors in the environment that can help to deal with cognitive load. The association model can be constructed using a neural network and/or deep machine learning algorithms. The system learns the risks of falling for various populations groups and the impact of cognitive load on the risk score.

During this phase the system also learns cognitive load baselines by identifying activities which impact cognitive load and their threshold for impacting motor functions such as posture, balance and gate, which contribute to fall risk. The system establishes baselines for various population groups based on factors such as mental and medical health conditions, medical history, accessibility issues (e.g., hearing, vision, mental), fitness level and physical impairments, as well as social conditions such as whether a person lives alone.

The system learns the predictive model for the risk of losing balance according to cognitive load. The system utilizes medical research, health records, and empirical fitness level data for building the model for predicting fall risk.

After building the general predictive model, the process proceeds to the system personalization or adaptation phase 520 in which a customized predictive model is constructed for the user in question. The system learns the person, so to speak. In this phase the system adjusts the association model regarding environment factors and cognitive load based on the user's personal preferences and individual effectiveness in applying various external factors.

In some embodiments, the users opt-in to the collection of the biometric data when installing or running the program. For example, when the program is launched for the first time, the system can provide the users with information about what data it will collect (e.g., heart rate data, blood pressure data, body temperature, etc.) and how it will use the data. The users are then provided with an option to opt-in to the data collection if they want to use the system. The collected user data can then be encrypted. If a user decides to opt-out of the system, the system can delete any personal user data collected for the user.

The system then adjusts the cognitive load baselines for the individual based on the person's activities and the impact of those activities on cognitive load and their thresholds for impacting the person's posture, balance and gait. Some users might have higher or lower thresholds than the general group population, and the relative impact of individual activities might vary from person to person.

The system evaluates the risk of falling for the person by applying the predictive risk-of-fall model to the person's profile and historical data, which is continually being updated.

During the system runtime phase 530 the system monitors the person's activities and cognitive load metrics. Activities can include, without limitation, working on a computer or electronic device, reading books, watching television, listening to music, talking on a telephone, etc. The system measures the volume of the activities for example using a time duration metric and/or simultaneity of activities metric when measuring cognitive load. From this the system evaluates the risk of falling score based on the cognitive load. The system identifies cognitive overload and increased risk score and applies smart home enhancements to assist the user to maintain balance.

Figure 6:
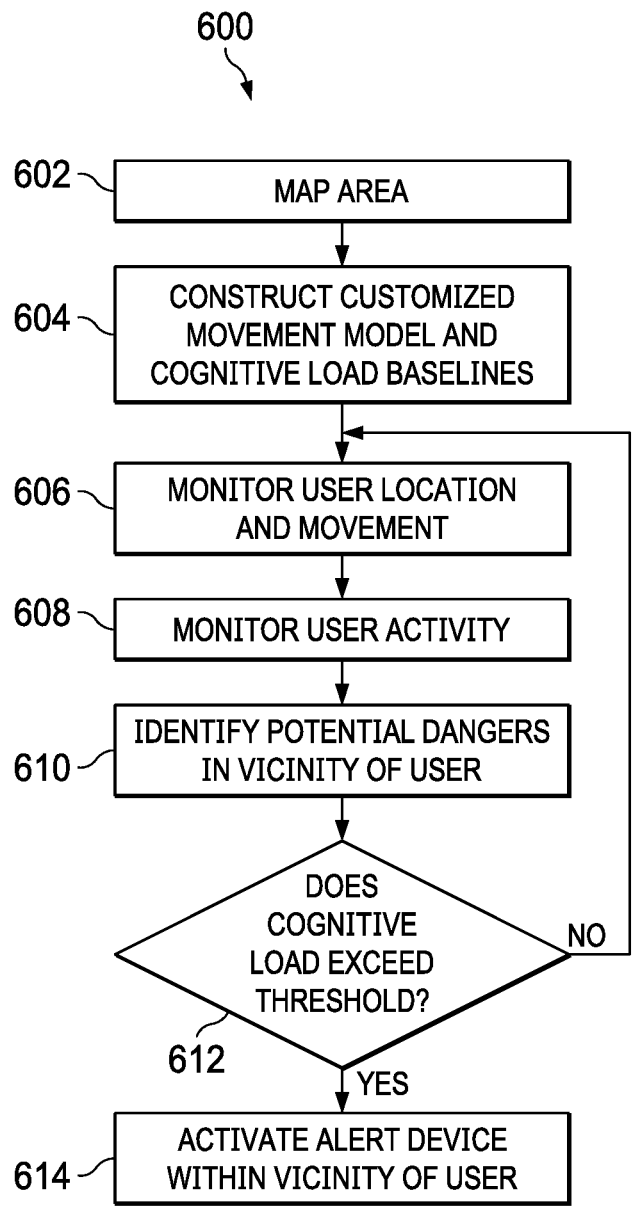
FIG. 6 is a flowchart depicting the operation of a cognitive load monitoring and alert system in accordance with illustrative embodiments.

FIG. 6 is a flowchart depicting the operation of a cognitive load monitoring and alert system in accordance with illustrative embodiments. Process 600 begins by mapping a predefined spatial area and identifying physical features in the spatial area that pose a fall risk (step 602). Next a customize movement model and cognitive load thresholds are established for the user (step 604).

User movement and location is continually monitored via a number of input devices (step 606), and user activity is monitored to determine cognitive load (step 608). Potential dangers and fall hazards are identified within a specified proximity to the user's current position (step 610).

If a fall hazard is detected within the vicinity of the user, the system determines if the user's cognitive load exceeds a predetermined threshold (step 612). If the cognitive load does not exceed the threshold, the system continues monitoring user activity and location. If the cognitive load does exceed the threshold, the system activates an alert device located within another specified proximity of the user to gain the user's attention regarding the hazard (step 614).

An example of the operation of the cognitive load monitoring system is an elderly individual, who has been recently discharged from an acute care hospital. The system evaluates her fall risk score as high. The system detects the individual preparing documents at a computer and applies cognitive baselines and detects a threshold being reached. The system adjusts the risk score and applies a high level of individual alerts for the individual. The system then detects the individual preparing to walk a dog and activates smart fixtures in the home and lights the staircase rails and the outside doorstep to help the individual avoid falling.

Another example is an elderly individual that is retired but is occasionally involved with local college research projects. Based on the individual's medical history, profile data, and fitness level the system evaluates the individual's fall risk score as low. The system detects the individual is increasingly working on a computer for research projects. Though the individual's cognitive load increases above a baseline it does not exceed the threshold. The system activates IoT devices to warn the individual to adjust the workload as a precautionary measure. The system might run background music during breaks to help the individual switch attention during multitasking.

Figure 7:
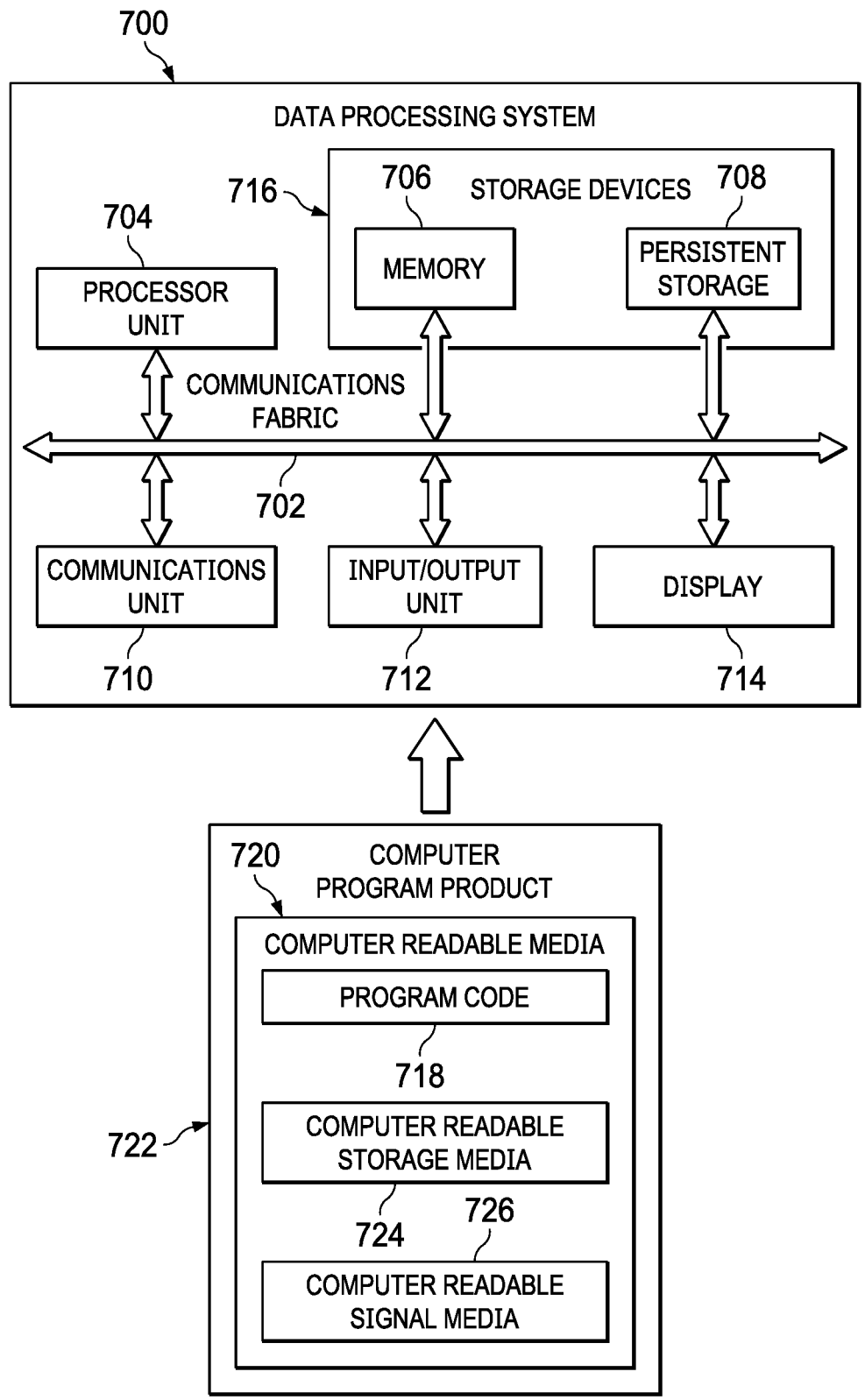
FIG. 7 is a diagram of a data processing system in accordance with an illustrative embodiment.

Turning to FIG. 7, a diagram of a data processing system is depicted in accordance with an illustrative embodiment. Data processing system 700 is an example of a system in which computer-readable program code or program instructions implementing processes of illustrative embodiments may be run. In this illustrative example, data processing system 700 includes communications fabric 702, which provides communications between processor unit 704, memory 706, persistent storage 708, communications unit 710, input/output unit 712, and display 714.

Processor unit 704 serves to execute instructions for software applications and programs that may be loaded into memory 706. Processor unit 704 may be a set of one or more hardware processor devices or may be a multi-processor core, depending on the particular implementation. Further, processor unit 704 may be implemented using one or more heterogeneous processor systems, in which a main processor is present with secondary processors on a single chip. As another illustrative example, processor unit 704 may be a symmetric multi-processor system containing multiple processors of the same type.

A computer-readable storage device is any piece of hardware that is capable of storing information, such as, for example, without limitation, data, computer-readable program code in functional form, and/or other suitable information either on a transient basis and/or a persistent basis. Further, a computer-readable storage device excludes a propagation medium. Memory 706, in these examples, may be, for example, a random-access memory, or any other suitable volatile or non-volatile storage device. Persistent storage 708 may take various forms, depending on the particular implementation. For example, persistent storage 708 may contain one or more devices. For example, persistent storage 708 may be a hard drive, a flash memory, a rewritable optical disk, a rewritable magnetic tape, or some combination of the above. The media used by persistent storage 708 may be removable. For example, a removable hard drive may be used for persistent storage 708.

Communications unit 710, in this example, provides for communication with other computers, data processing systems, and devices via network communications unit 710 may provide communications using both physical and wireless communications links. The physical communications link may utilize, for example, a wire, cable, universal serial bus, or any other physical technology to establish a physical communications link for data processing system 700. The wireless communications link may utilize, for example, shortwave, high frequency, ultra-high frequency, microwave, wireless fidelity (WIFI), Bluetooth technology, global system for mobile communications (GSM), code division multiple access (CDMA), second-generation (2G), third-generation (3G), fourth-generation (4G), 4G Long Term Evolution (LTE), LTE Advanced, or any other wireless communication technology or standard to establish a wireless communications link for data processing system 700.

Input/output unit 712 allows for the input and output of data with other devices that may be connected to data processing system 700. For example, input/output unit 712 may provide a connection for user input through a keypad, keyboard, and/or some other suitable input device. Display 714 provides a mechanism to display information to a user and may include touch screen capabilities to allow the user to make on-screen selections through user interfaces or input data, for example.

Instructions for the operating system, applications, and/or programs may be located in storage devices 716, which are in communication with processor unit 704 through communications fabric 702. In this illustrative example, the instructions are in a functional form on persistent storage 708. These instructions may be loaded into memory 706 for running by processor unit 704. The processes of the different embodiments may be performed by processor unit 704 using computer-implemented program instructions, which may be located in a memory, such as memory 706. These program instructions are referred to as program code, computer-usable program code, or computer-readable program code that may be read and run by a processor in processor unit 704. The program code, in the different embodiments, may be embodied on different physical computer-readable storage devices, such as memory 706 or persistent storage 708.

Program code 718 is located in a functional form on computer-readable media 720 that is selectively removable and may be loaded onto or transferred to data processing system 700 for running by processor unit 704. Program code 718 and computer-readable media 720 form computer program product 722. In one example, computer-readable media 720 may be computer-readable storage media 724 or computer-readable signal media 726. Computer-readable storage media 724 may include, for example, an optical or magnetic disc that is inserted or placed into a drive or other device that is part of persistent storage 708 for transfer onto a storage device, such as a hard drive, that is part of persistent storage 708. Computer-readable storage media 724 also may take the form of a persistent storage, such as a hard drive, a thumb drive, or a flash memory that is connected to data processing system 700. In some instances, computer-readable storage media 724 may not be removable from data processing system 700.

Alternatively, program code 718 may be transferred to data processing system 700 using computer-readable signal media 726. Computer-readable signal media 726 may be, for example, a propagated data signal containing program code 718. For example, computer-readable signal media 726 may be an electro-magnetic signal, an optical signal, and/or any other suitable type of signal. These signals may be transmitted over communication links, such as wireless communication links, an optical fiber cable, a coaxial cable, a wire, and/or any other suitable type of communications link. In other words, the communications link and/or the connection may be physical or wireless in the illustrative examples. The computer-readable media also may take the form of non-tangible media, such as communication links or wireless transmissions containing the program code.

In some illustrative embodiments, program code 718 may be downloaded over a network to persistent storage 708 from another device or data processing system through computer-readable signal media 726 for use within data processing system 700. For instance, program code stored in a computer-readable storage media in a data processing system may be downloaded over a network from the data processing system to data processing system 700. The data processing system providing program code 718 may be a server computer, a client computer, or some other device capable of storing and transmitting program code 718.

The different components illustrated for data processing system 700 are not meant to provide architectural limitations to the manner in which different embodiments may be implemented. The different illustrative embodiments may be implemented in a data processing system including components in addition to, or in place of, those illustrated for data processing system 700. Other components shown in FIG. 7 can be varied from the illustrative examples shown. The different embodiments may be implemented using any hardware device or system capable of executing program code. As one example, data processing system 700 may include organic components integrated with inorganic components and/or may be comprised entirely of organic components excluding a human being. For example, a storage device may be comprised of an organic semiconductor.

As another example, a computer-readable storage device in data processing system 700 is any hardware apparatus that may store data. Memory 706, persistent storage 708, and computer-readable storage media 724 are examples of physical storage devices in a tangible form.

In another example, a bus system may be used to implement communications fabric 702 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 706 or a cache such as found in an interface and memory controller hub that may be present in communications fabric 702.

The present invention may be a system, a method, and/or a computer program product. The computer program product may include a computer-readable storage medium or media having computer-readable program instructions thereon for causing a processor to carry out aspects of the present invention.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer-readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer-readable program instructions by utilizing state information of the computer readable program instructions to personalize the electronic circuitry, in order to perform aspects of the present invention.

These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer-readable medium that can direct a computer, other programmable data processing apparatus, or other devices to function in a particular manner, such that the instructions stored in the computer-readable medium produce an article of manufacture including instructions which implement the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Furthermore, it should be understood that embodiments discussed herein are not limited to the particular features and processing steps shown. The descriptions provided herein are not intended to encompass all of the steps that may be used to form a functional integrated circuit device. Certain steps that are commonly used in fabricating such devices are purposefully not described herein for economy of description.

The flowchart and diagrams in the figures illustrate the method and resulting architecture according to embodiments of the present disclosure. In this regard, each block in the flowchart or structural diagrams may represent a step or partial step, which comprise one or more procedures for implementing the illustrative embodiments. In some alternative implementations, the functions noted in the block may occur out of the order noted in the figures. For example, two blocks shown in succession may, in fact, be performed substantially concurrently, or the blocks may sometimes be performed in the reverse order, depending upon the functionality involved.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A method for preventing falls and accidents, comprising:
    monitoring, by a number of input devices, a user's location movement;
    monitoring, by the number of input devices, the user's activities;

identifying, by a number of processors in communication with the number of input devices, a potential danger within a first specified proximity of the user;

determining, by the number of processors in communication with the number of input devices in response to determining the potential danger, if the user's current activity indicates a cognitive load of the user that exceeds a predefined threshold;

in response to determining that the user's cognitive load exceeds the predefined threshold, activating, by the number of processors, a number of devices within a second specified proximity of the user to alert the user of the potential danger; and constructing a predictive model that identifies user activities that impact the user's cognitive load and establishes associated cognitive load thresholds correlated with changes in posture, balance, and risk of falls of the user.

2. The method of claim 1, further comprising:

constructing a customized movement model of the user from the predictive model that establishes movement baselines and identifies the cognitive load thresholds that alter the user's movements from the movement baselines; and adjusting the movement baselines based on the user's current activity and an impact of the user's current activity on the user's cognitive load.

3. The method of claim 1, wherein the predictive model correlates risk of falls with at least one of population data, medical history and fitness levels; and further comprising:

altering a manner in which information is delivered to the user based on the user's cognitive load without increasing the user's cognitive load.

4. The method of claim 3, further comprising constructing a customized risk model of the user from the predictive model based on at least one of:
- age;
- medical history;
- medication use;
- living arrangements; and
- fitness level.

5. The method of claim 1, further comprising establishing a risk map for a predefined spatial area that identifies physical features in the spatial area that pose a fall risk.

6. The method of claim 1, wherein the cognitive load is determined by monitoring:
- biometric sensors;
- user's use of electronic devices;
- cameras; and
- motion sensors.

7. The method of claim 1, wherein the number of devices activated to alert the user include at least one device in an environment of the user and at least one other device used by the user, and comprise:
- an interface that requests the user to perform a task; and
- an internet enabled appliance.

8. A system for preventing falls and accidents, comprising:
- a bus system;
- a storage device connected to the bus system, wherein the storage device stores program instructions; and
- a number of processors connected to the bus system, wherein the number of processors execute the program instructions to:
  - monitor a user's location movement, and cognitive load from data provided by a number of input devices;
  - monitor the user's activities from data provided by the number of input devices;
  - identify, according to data provided by the number of input devices, a potential danger within a first specified proximity of the user;
  - determine, according to data provided by the number of input devices in response to determining the potential danger, if the user's current activity indicates the cognitive load of the user that exceeds a predefined threshold;
  - in response to determining that the user's cognitive load exceeds the predefined threshold, activate a number of devices within a second specified proximity of the user to alert the user of the potential danger; and
  - alter a manner in which information is delivered to the user based on the user's cognitive load without increasing the user's cognitive load;
- a predictive model that identifies user activities that impact the user's cognitive load and establishes associated cognitive load thresholds correlated with changes in posture, balance, and risk of falls of the user;
- a customized movement model of the user that establishes movement baselines and identifies the cognitive load thresholds that alter the user's movements from the movement baselines, and wherein the number of processors execute the program instructions to:
  - adjust the movement baselines based on the user's current activity and an impact of the user's current activity on the user's cognitive load.

9. The system of claim 8, further comprising establishing a risk map for a predefined spatial area that identifies physical features in the spatial area that pose a fall risk.

10. The system of claim 8, wherein the cognitive load is determined by monitoring:
- biometric sensors;
- user's use of electronic devices;
- cameras; and
- motion sensors.

11. The system of claim 8, wherein the number of devices activated to alert the user include at least one device in an environment of the user and at least one other device used by the user, and comprise at least one of:
- an interface that requests the user to perform a task; and
- an internet enabled appliance.

12. A computer program product for preventing falls and accidents, comprising, the computer program product comprising a non-volatile computer readable storage medium having program instructions embodied therewith, the program instructions executable by a computer to cause the computer to perform the steps of:

monitoring a user's location, movement, and cognitive load from data provided by a number of input devices;

monitoring the user's activities from data provided by the number of input devices;

identifying, according to data provided by the number of input devices, a potential danger within a first specified proximity of the user;

determining, according to data provided by the number of input devices in response to determining the potential danger, if the user's current activity indicates the cognitive load that exceeds a predefined threshold;

in response determining that the user's cognitive load exceeds the predefined threshold, activating a number of devices within a second specified proximity of the user to alert the user of the potential danger;

identifying, by a predictive model, user activities that impact the user's cognitive load and establishes associated cognitive load thresholds correlated with changes in posture, balance, and risk of falls of the user;

altering a manner in which information is delivered to the user based on the user's cognitive load without increasing the user's cognitive load;

a customized movement model of the user that establishes movement baselines and identifies the cognitive load thresholds that alter the user's movements from the movement baselines; and wherein the program instructions executable by the computer to cause the computer to perform a step of:

adjusting the movement baselines based on the user's current activity and an impact of the user's current activity on the user's cognitive load.

13. The computer program product of claim 12, wherein the predictive model correlates risk of falls with at least one of population data, medical history and fitness levels.

14. The computer program product of claim 12, further comprising a customized risk model of the user based at least one of:

age;

medical history;

medication use;

living arrangements; and fitness level.

15. The computer program product of claim 12, further comprising a risk map for a predefined spatial area that identifies physical features in the spatial area that pose a fall risk.

16. The method of claim 1, wherein the user's current activity is using a mobile device by the user, and wherein the number of devices activated to alert the user of the potential damage and the number of input devices that are monitored is the mobile device.

17. The system of claim 8, wherein the user's current activity is using a mobile device by the user, and wherein the number of devices activated to alert the user of the potential damage and the number of input devices that are monitored is the mobile device.

* * * * *